US010159948B2

(12) United States Patent
Seaward et al.

(10) Patent No.: US 10,159,948 B2
(45) Date of Patent: Dec. 25, 2018

(54) DRUM AGITATION ACTUATOR HAVING A SERIES OF OFFSET MAGNETS

(71) Applicant: 3P Innovation Limited, Warwick, Warwickshire (GB)

(72) Inventors: David Seaward, Warwick (GB); Thomas Bailey, Warwick (GB)

(73) Assignee: 3P Innovation Limited, Warwick (GB)

( * ) Notice: Subject to any disclaimer, the term of this patent is extended or adjusted under 35 U.S.C. 154(b) by 566 days.

(21) Appl. No.: 14/772,565

(22) PCT Filed: Mar. 4, 2014

(86) PCT No.: PCT/GB2014/050626
§ 371 (c)(1),
(2) Date: Sep. 3, 2015

(87) PCT Pub. No.: WO2014/135853
PCT Pub. Date: Sep. 12, 2014

(65) Prior Publication Data
US 2016/0008779 A1    Jan. 14, 2016

(30) Foreign Application Priority Data

Mar. 4, 2013 (GB) .................................. 1303806.2

(51) Int. Cl.
*B01F 13/08* (2006.01)
*B01F 11/00* (2006.01)
(Continued)

(52) U.S. Cl.
CPC ............ *B01F 13/08* (2013.01); *A61M 5/284* (2013.01); *B01F 3/04978* (2013.01);
(Continued)

(58) Field of Classification Search
CPC ....................................................... B01F 13/08
See application file for complete search history.

(56) References Cited

U.S. PATENT DOCUMENTS 2,184,152 A * 12/1939 Saffir .................. B65D 81/3277
206/222
3,219,318 A * 11/1965 Hershler ............. B01F 13/0809
204/155
(Continued)

FOREIGN PATENT DOCUMENTS

EP      0188981 A1    7/1986
EP      0652019 A1    5/1995
(Continued)

OTHER PUBLICATIONS

UK Intellectual Propery Office, Search Report under Section 17(5) to UK Patent Application GB1303806.2, dated Jul. 26, 2013, UK.
(Continued)

*Primary Examiner* — Abbas Rashid
(74) *Attorney, Agent, or Firm* — NK Patent Law

(57) ABSTRACT

A mixing apparatus (130) for a syringe (110), the mixing apparatus comprising a dock (134) configured to receive the syringe and having an agitation component actuator (132) integral to the dock configured for magnetically coupling to an agitation component (136) of a magnetic material located within a chamber of said syringe, and configured for manipulation of said agitation component within said chamber when coupled; wherein the actuator is in the form of a drum having a series of magnets attached thereto offset in relation to one another so as to manipulate said actuation component in a reciprocating motion upon rotation of the drum.

8 Claims, 10 Drawing Sheets

(51) Int. Cl.
  *B01F 13/00* (2006.01)
  *B01F 15/00* (2006.01)
  *B01F 15/02* (2006.01)
  *B01F 3/04* (2006.01)
  *A61M 5/28* (2006.01)
  *A61M 5/178* (2006.01)

(52) U.S. Cl.
  CPC ...... *B01F 11/0054* (2013.01); *B01F 11/0082* (2013.01); *B01F 13/003* (2013.01); *B01F 13/0818* (2013.01); *B01F 15/00253* (2013.01); *B01F 15/00285* (2013.01); *B01F 15/00376* (2013.01); *B01F 15/00383* (2013.01); *B01F 15/00409* (2013.01); *B01F 15/0279* (2013.01); *A61M 5/178* (2013.01); *B01F 2215/0032* (2013.01)

(56) References Cited

U.S. PATENT DOCUMENTS

| | | | |
|---|---|---|---|
| 3,789,670 A | 2/1974 | Rosenwald | |
| 4,159,570 A | 7/1979 | Baskas et al. | |
| 4,208,133 A | 6/1980 | Korte-Jungermann | |
| 5,352,036 A | 10/1994 | Haber et al. | |
| 6,382,827 B1 * | 5/2002 | Gebrian | B01F 13/0818 366/274 |
| 6,706,020 B1 | 3/2004 | Urich | |
| 6,880,384 B2 * | 4/2005 | Hvidtfeldt | B01F 11/0017 422/417 |
| 7,484,880 B2 * | 2/2009 | Cleveland | B01F 13/0818 366/273 |
| 9,855,536 B2 * | 1/2018 | Nguyen | B01F 13/08 |
| 2003/0029254 A1 | 2/2003 | Hvidtfeldt et al. | |
| 2003/0126914 A1 | 7/2003 | Hvidtfeldt et al. | |
| 2005/0238540 A1 * | 10/2005 | Swon | B01F 11/0082 422/561 |
| 2009/0112157 A1 | 4/2009 | Jessop | |
| 2014/0376328 A1 * | 12/2014 | Ikushima | B01F 13/0863 366/191 |

FOREIGN PATENT DOCUMENTS

| | | |
|---|---|---|
| GB | 2338428 A | 12/1999 |
| WO | 03053494 A2 | 7/2003 |
| WO | 2004057304 A1 | 7/2004 |
| WO | 2011103384 A1 | 8/2011 |

OTHER PUBLICATIONS

European Patent Office, International Search Report to PCT Patent Application PCT/GB2014/050626, dated May 15, 2014.

* cited by examiner

DRUM AGITATION ACTUATOR HAVING A SERIES OF OFFSET MAGNETS

The present invention relates to a mixing apparatus for a syringe, to a syringe and to a method of mixing a substance in a syringe.

It is known to mix the contents of a syringe or a syringe cartridge to ensure that they are properly combined prior to injecting them from the syringe. This is of particular importance where a substance may have separated whilst in the syringe, or where more than one substance is combined in a chamber of the syringe shortly before injection. Increasingly, more viscous substances and suspensions are being injected from syringes, and it is important to ensure that proper mixing of these has taken place.

One particular class of medicaments are large molecule biologic drug substances. These typically require injection as the delivery route into the body, and are not shelf stable in aqueous solution. To avoid the expense (and impracticality) of cold chain logistics, this has led to growth in dual chamber reconstitution syringes whereby the drug substance is stored as a powder and mixed shortly prior to use with a diluent. When in powdered form the drug substance does not readily dissolve or enter suspension quickly or uniformly. Mixing is normally accomplished by the substance administrator bringing the powder and diluent together and manually shaking the resultant mixture until it is subjectively well mixed.

The amount of shaking to which the syringe contents are subjected varies from administrator to administrator in terms of length of shaking time, shaking speed and shaking direction. There is no regulation of mixing; nor is there any assessment of whether full mixing has taken place; and it is therefore possible for the syringe contents to not be properly mixed prior to injection. Due to their complexity such products are generally administered by healthcare professionals in a hospital environment. However, self injection at home will increasingly be required in order to manage healthcare costs.

Dual chamber injection devices hold two different constituents apart in separate chambers until shortly prior to administration. These systems are known. Systems using this concept are described in U.S. Pat. Nos. 4,861,335, 5,137,511, 5,171,220, 5,281,198, 5,364,369, 5,569,192, 5,685,846, 5,779,668, 5,817,056, 5,971,953, 6,902,543 and PCT 99/17820.

These devices rely on the rapid solubility of the medicament into the diluent, or the rapid mixing of two liquids. Many compounds demonstrate poor solubility or poor mixing. Enhanced static mixing systems have been developed as described in U.S. Pat. Nos. 5,566,729 and 7,678,073.

The spinning of a stirring element within a medicament container such as a vial is well known and is often achieved by use of spinning magnets or directly by a motor driven impeller.

Dissolving or suspending particulates in liquids, emulsifying two liquids or mixing liquids can be accomplished using readily available magnetic horizontal spin stirrers. A method of moving a stirring element with alternating magnetic fields generated by electromagnets is described in U.S. Pat. No. 4,080,663. Mechanical movement of permanent magnets, via an electric motor, to create a moving magnetic field which interacts with a stirring element is described in U.S. Pat. No. 6,176,609. U.S. Pat. No. 6,872,362 describes a vial mixing system using magnetic element spun by an electrical motor.

These mixing systems spin a stirring element at the bottom of the container. The present applicant has recognised this is not ideal for an injectable application, where the complete mixing chamber volume would ideally be swept by a stirring element. In addition the stirring element takes up a volume which may prevent the plunger from reaching the end of the syringe: this in turn prevents the entire medicament being expelled during administration.

An example of such a syringe as described in the referenced prior art is shown in FIGS. 1a to 1c. The syringe 10 has a first, mixing, chamber 12 and a second chamber 14, each chamber 12, 14 containing ingredients to be combined before being expelled from the syringe 10. The chambers 12, 14 may be integral to the syringe 10, or may be defined by cartridges held within the syringe 10. The first chamber 12 is distal an outlet end 10a of the syringe, and the second chamber 14 is proximal the outlet end 10a.

The first chamber 12 is configured to hold powder or liquid, and the second chamber 14 is configured to hold liquid. The chambers 12, 14 are configured to keep their contents separate from one another whilst in the first position shown in FIG. 1a, so that the contents remain inactive. Each chamber 12, 14 has a seal 16 at its end proximal the other chamber 12, 14 to retain the chamber contents within each respective chamber 12, 14.

A double-ended needle 18 is located within the syringe 10 between the seals 16. The needle 18 defines a passageway 20. As shown in FIG. 1b, when the chamber contents are to be combined, the first chamber 12 is moved (e.g. by a plunger, not shown) towards the second chamber 14, so that the needle 18 pierces the seals 16. The chambers 12, 14 are thus connected by the passageway 20, and the chamber contents can move between the chambers 12, 14.

In order to combine the chamber contents, the first chamber 12 is moved further towards the second chamber 14. The seal 16 of the second chamber 14 is moved by the first chamber 12 to decrease the volume of the second chamber 14, acting as a plunger. Liquid is thus forced from the second chamber 14 along the passageway 20 to the first chamber 12, until the seal 16 reaches the end of the second chamber 14 and the second chamber is substantially empty, as shown in FIG. 1c. Substantially all of the contents of the chambers 12, 14 is combined in the first chamber 12, ready for mixing and expulsion from the syringe.

It can be seen that the previously separated syringe contents will require effective mixing. When used by unskilled operators, and/or in remote, rural areas, mixing of the substances is likely to be uncontrolled and unlikely to be assessed.

It will also be appreciated that the powder can be placed in chamber 14 and liquid in chamber 12 as described in U.S. Pat. No. 3,489,147, U.S. Pat. No. 3,464,412 and U.S. Pat. No. 3,326,215.

There is a need for an improved mixing apparatus for a syringe.

An aspect of the present invention provides an improved system for mixing medicaments within a syringe or within syringe cartridges whereby substantially the complete volume is swept by an agitation element.

According to a first aspect of the present invention there is provided a mixing apparatus for a syringe, the mixing apparatus comprising a dock configured to receive the syringe and having an agitation component actuator integral to the dock configured for magnetically coupling to an agitation component of a magnetic material located within a chamber of said syringe, and configured for manipulation of said agitation component within said chamber when coupled such that the actuator is coupled to said agitation component when said syringe is received by the dock, wherein the actuator is in the form of a drum having a series of magnets attached thereto offset in relation to one another so as to manipulate said actuation component in a reciprocating motion upon rotation of the drum.

The dock is a convenient way of supporting the syringe during mixing, and ensures that mixing takes place correctly, as said agitation component and the actuator are properly coupled. The recess in the dock ensures proper coupling of said agitation component and the actuator, and makes the apparatus easy and convenient to use. The use of a drum with magnets mounted thereon provides and effective way of causing the agitation component to substantially fully sweeping the chamber to improve mixing.

Said chamber may define a longitudinal axis, and the actuator may be configured to rotate said agitation component about a longitudinal axis. The combination of longitudinal and rotational movement may improve mixing, whilst at the same time minimises the propensity for frothing or foaming of liquids. Foamed liquids should not be injected, and it can typically taken 15-30 minutes for foam, once formed, to subside.

The series of magnets may be configured such that opposing poles are proximal one another to induce spinning of the agitation component. This has been found to be an effective way of generating rotation/spinning of the agitation component.

Preferably, the series of magnets form a V-shape arrangement or are arranged helically around the drum.

Said chamber may define a longitudinal axis, and the actuator may be configured to manipulate said agitation component in a reciprocating motion substantially parallel with said longitudinal axis.

Reciprocation of the agitation component along said chamber allows the full length of said chamber to be swept, improving mixing.

The present invention thus provides a cost effective method of mixing a large swept volume of any mixing chamber. The agitation component can be moved along the longitudinal axis of a syringe mixing chamber and/or spun when placed in a separate docking station.

The axis of the drum is preferably substantially parallel to that of the chamber.

Preferably, the mixing apparatus further comprises a control system configured to control at least one of the following parameters: speed of movement of said agitation component; direction of movement of said agitation component; force or torque of said agitation component and length of mixing time.

The apparatus self-regulates mixing via the control system, so that the required amount of mixing takes place without the need for skill or specialist knowledge on the part of the operator. The mixing apparatus is also quicker, more consistent and more effective than manual mixing. The parameters may also be controlled to further minimise frothing or foaming.

The control system may comprise a memory configured to store control information for one or more different substances that may be held within said chamber, and/or may be configured to adjust the or each parameter according to the substance within said chamber.

Different substances can thus be subjected to the appropriate amount of mixing, again without the need for skill or specialist knowledge from the operator. The dock may be configured to retain said syringe until mixing is complete. This prevents removal of the syringe before mixing has been completed.

In one embodiment, the actuator may be configured for attachment to a chamber of a syringe. The mixing apparatus may further comprise a sensor arrangement connected to the control arrangement and configured to detect a characteristic of the contents of said chamber in order to determine the level of mixing of the contents.

The sensor determines whether or not further mixing is required, and the control system controls mixing accordingly.

The sensor arrangement may be configured to detect a characteristic of said chamber contents when said syringe is received by the dock, and/or may be integral to the dock.

The sensor arrangement being integral to the dock ensures that a syringe is correctly located with respect to the sensor arrangement, and that the apparatus is compact and easy to use.

The actuator may comprise a magnetic field configured for coupling to an agitation component of a magnetic material. The magnetic field may be provided by one or more electromagnets.

This allows controlled remote mixing of the substance.

In one embodiment, the actuator may comprise a motor.

The arrangement of an agitation component extending from said chamber for coupling to a mechanical drive system such as a motor provides a simple and effective form of mixing that is easily controlled.

According to a second aspect of the present invention, there is provided an assembly comprising a mixing apparatus according to the first aspect of the invention and a syringe for use therewith, the syringe comprising a chamber, a plunger configured to expel contents of the chamber from the chamber, and an agitation component located within the chamber. The shape of the agitation component may correspond at least in part to the shape of the plunger.

The plunger may define a recess configured to receive at least part of the agitation component. The recess may be configured to substantially wholly receive the agitation component.

Without such a recess, the plunger can be prevented from reaching the end of the chamber by the agitation component, which can become trapped between the plunger and an outlet end of the chamber. In such a case it is difficult to expel all of a substance from the chamber, leading to waste and, potentially, incorrect dosage. The recess defined by the plunger is configured to at least partially receive the agitation component, allowing the plunger to get closer to the outlet end of the chamber, reducing waste and the chance of incorrect dosage.

The agitation component may define a recess configured to receive at least part of the plunger.

Again, this arrangement reduces waste and the chance of incorrect dosage.

The agitation component may be configured to fit within or conform to a neck of the chamber. This arrangement reduces waste and the chance of incorrect dosage.

The mixing apparatus may be for use with a mixing chamber of a syringe having first and second chambers containing substances to be combined in the mixing chamber.

The mixing apparatus is of particular use in such a syringe, as disparate substances must be well combined prior to injection. Once of the substances may be a powder and the other a liquid, which require particularly effective and well-regulated mixing.

Said first chamber may be distal an outlet end of said syringe and said second chamber may be proximal said outlet end of said syringe, and wherein the agitation component may be configured for location within said first chamber.

This arrangement allows simple arrangement of the agitation component extending from the syringe for manipulation.

The agitation component may have a coating of a material suitable for contact with pharmaceutical substances.

This prevents the magnetic material of the agitation component, which may not be compatible with pharmaceutical substances, from coming into contact with them. The agitation component may be substantially circular in cross-section. This shape advantageously corresponds to that of standard syringes. The agitation component may be a spheroid, for example it may be an ellipsoid.

The agitation component may define at least one bore extending therethrough.

Having one or more bores extending through the agitation component allows the chamber contents to move through the agitation component, so that the agitation component can move freely through said chamber, improving mixing.

According to a third aspect of the present invention, there is provided a method of mixing a substance within a chamber of a syringe, the method comprising:
 a) providing a syringe with an agitation component and a mixing apparatus as described above;
 b) coupling the agitation component to the actuator; and
 c) using the actuator to manipulate the agitation component in a reciprocating motion.

The method may further comprise the step of, prior to step a) and/or step b):
 d) providing a control system configured to control at least one of the following parameters: speed of movement of said agitation component; direction of movement of said agitation component; force or torque applied by said agitation component and length of mixing time;
 e) programming the control system to, during step c), move the agitation component at a particular speed; and/or in a particular direction of movement; and/or with a particular force or torque; and/or for a particular length of time, depending on the substance to be mixed.

The methods may further comprise the step of:
 f) providing a sensor arrangement connected to the control system and configured to detect a characteristic of the contents of said chamber in order to determine the level of mixing of the contents and, during step c):
 g) taking account of feedback from the sensor arrangement.

According to a fourth aspect of the present invention there is provided a mixing apparatus for a syringe, the mixing apparatus comprising:
 an actuator configured for coupling to an agitation component located within a chamber of said syringe, and configured for manipulation of said agitation component within said chamber when coupled;
 wherein the mixing apparatus further comprises a control system configured to control at least one of the following parameters: speed of movement of said agitation component; direction of movement of said agitation component; force or torque of said agitation component and length of mixing time.

According to a fifth aspect of the present invention, there is provided a syringe or injector comprising a chamber and an agitation component located within the chamber; the agitation component being configured for coupling to an agitation component actuator; and the syringe comprising a plunger configured to expel a substance from the chamber, wherein the shape of the agitation component corresponds at least in part to the shape of the plunger or a neck of the syringe chamber.

The plunger may define a recess configured to receive at least part of the agitation component. The recess may be configured to substantially wholly receive the agitation component.

Without such a recess, the plunger can be prevented from reaching the end of the chamber by the agitation component, which can become trapped between the plunger and an outlet end of the chamber. In such a case it is difficult to expel all of a substance from the chamber, leading to waste and, potentially, incorrect dosage. The recess defined by the plunger is configured to at least partially receive the agitation component, allowing the plunger to get closer to the outlet end of the chamber, reducing waste and the chance of incorrect dosage.

The agitation component may define a recess configured to receive at least part of the plunger.

Again, this arrangement reduces waste and the chance of incorrect dosage.

The mixing apparatus or the syringe may further comprise an agitation component.

A sixth aspect of the present invention provides a mixing apparatus for a syringe, the mixing apparatus comprising: an agitation component actuator configured for coupling to an agitation component located within a chamber of said syringe, and configured for manipulation of said agitation component within said chamber when coupled; wherein the actuator is configured to manipulate said actuation component in a reciprocating motion. The sixth aspect may optionally include the preferred features of the other aspects of the invention Other aspects and preferred features of the invention will be readily apparent from the claims and following description of preferred embodiments made, by way of example only, with reference to the following drawings, in which:

Figure 1A:
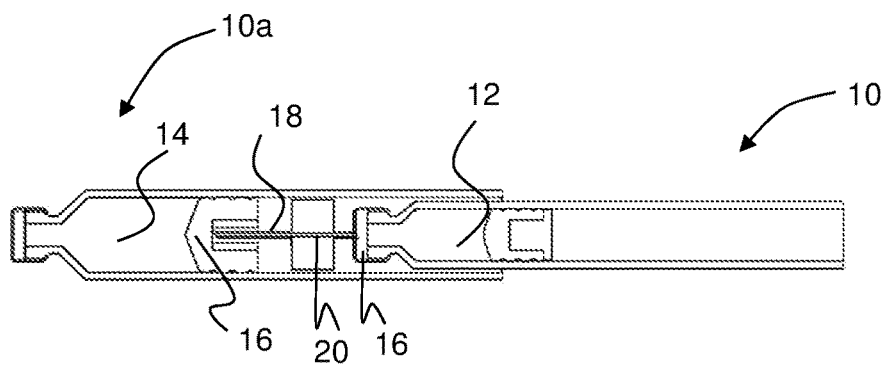
FIG. 1a is a cross-sectional view of a known syringe in a first position.
Figure 1B:
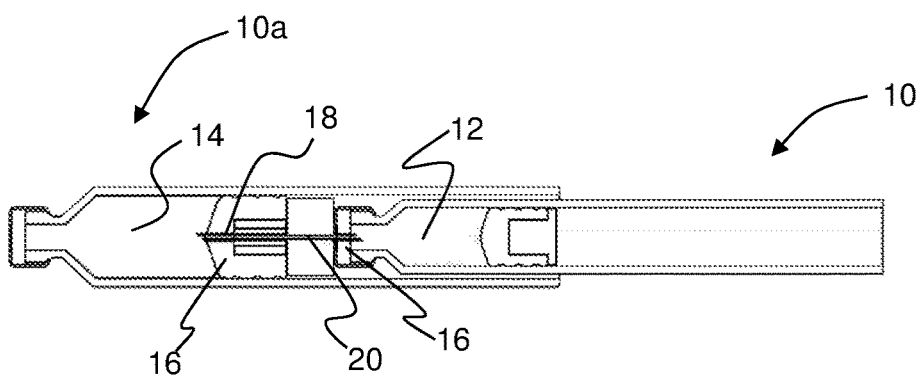
FIG. 1b is a cross-sectional view of the syringe of FIG. 1b in a second position.
Figure 1C:
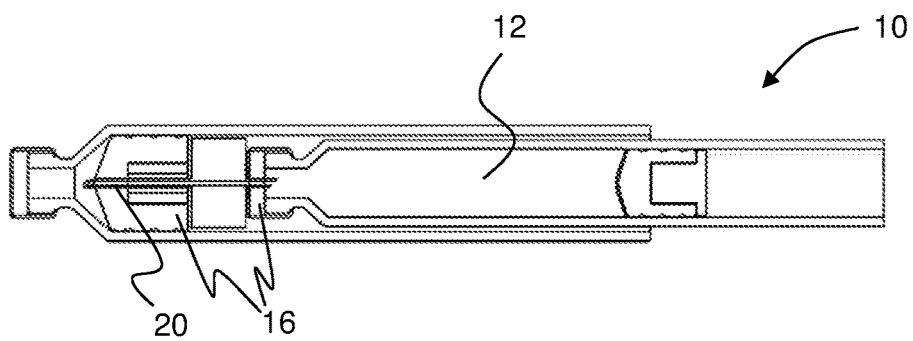
FIG. 1c is a cross-sectional view of the syringe of FIGS. 1a and 1b in a third position.
Figure 2:
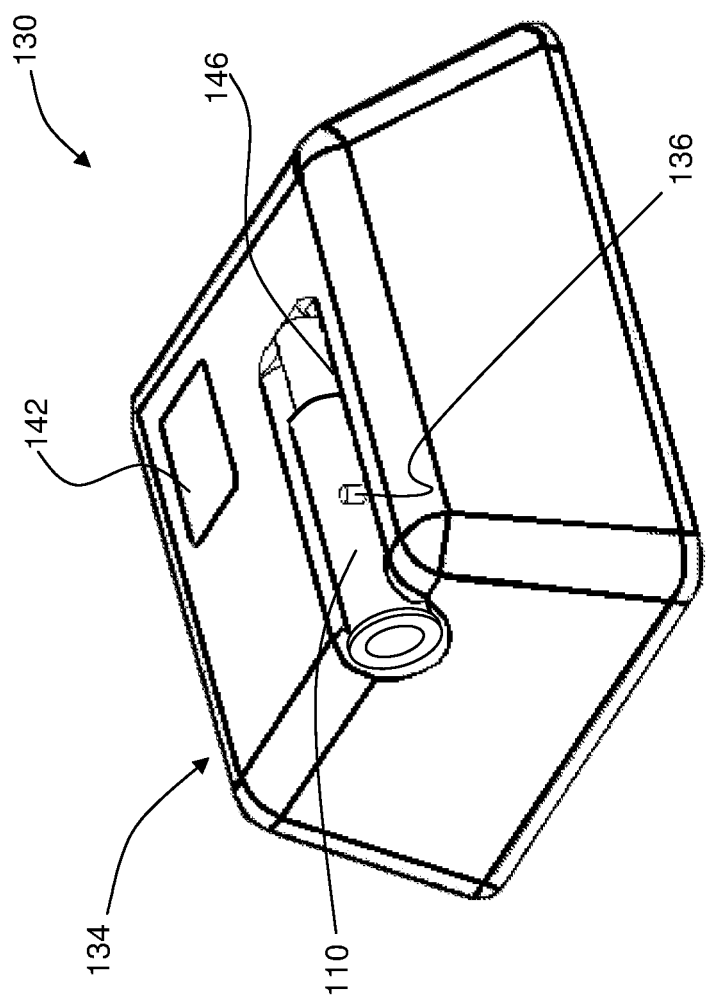
FIG. 2 is a perspective view of a mixing apparatus according to a first embodiment of the present invention.

A mixing apparatus 130 for a syringe 110 having a longitudinal axis A-A is shown in FIGS. 2 to 6. The mixing apparatus 130 has an agitation component actuator 132 housed within a dock 134, and an agitation component 136 intended for location in the mixing chamber 112 of the syringe 110.

The actuator 132 is coupled to the agitation component 136 in order to manipulate the agitation component 136 to move within the chamber 112 and carry out mixing of the chamber contents.

The mixing apparatus 130 also includes a control system 138 housed within the dock 134. The control system 138 is shown in schematic form in FIG. 5. The control system 138 includes a processor 139 and a memory 140 and is connected to the actuator 132, and through the actuator 132 controls movement of the agitation component 136 within the chamber. The control system 138 controls speed and direction of movement of the agitation component 136 (i.e. rate of mixing), force or torque applied by the agitation component 136 and length of mixing time. Mixing of the chamber contents is thus regulated, so that an appropriate amount of mixing takes place.

The memory 140 holds information regarding the mixing requirements of one or more substances for which the syringe 110 may be used. A particular mixing program can be manually selected depending on the syringe contents, without the need for specialist knowledge on the part of the operator. The dock 134 has an information display 142 configured to show options for program selection and a series of buttons (not shown) for selecting the appropriate program.

The dock 134 includes an attachment arrangement 146 configured to support the syringe 110 during mixing. In this embodiment the dock 134 defines a recess 146 for receiving the syringe 110 in a substantially horizontal position, although in alternative embodiments other types of recess or other types of attachment arrangement 146 may be provided, e.g. one or more clips, or an adjustable clamp configured to receive syringes of different sizes. The recess 146 can be adapted for different sizes of syringe 110 with removable inserts (not shown), so that the mixing apparatus 130 is suitable for different syringe sizes and types.

In an alternative embodiment (not shown) the recess 146 is configured for positive engagement with a syringe. That is, the recess 146 is configured to receive a particular type and/or size of syringe only, in order to prevent the wrong syringe being used. The recess 146 may be configured to detect the type of syringe 110 attached, and the control system 138 may automatically select a suitable mixing program based on the type of syringe 110. The dock 134 may be configured to retain the syringe 110 in the dock 134 until mixing is complete, to prevent removal of the syringe 110 before completion of mixing.

The mixing apparatus 130 also includes a sensor 150, which in this embodiment is housed in the dock 134. The sensor 150 is configured to measure the level of mixing of the chamber contents that has taken place, for example by detecting the concentration or turbidity of the chamber contents. In this embodiment the sensor 150 is an infra red sensor, which in this embodiment is configured to measure rate of change or variability of turbidity. In alternative embodiments other types of sensor may be used. For example, a near infra red sensor could be used to measure chemical composition of the chamber contents, or viscosity of the chamber contents may be measured by feedback from the agitation component 136 to the actuator 132, or concentration may be measured. The control system 138 automatically adjusts the speed of movement of said agitation component; direction of movement of said agitation component; force or torque applied by said agitation component or length of mixing time according to the sensor 150 readings, until a satisfactory level of mixing is achieved. In an alternative embodiment, the level of mixing is displayed on the information display 142 so that the operator can easily determine whether further mixing is required.

The actuator 132 is arranged within the dock 134 such that when the syringe 110 is supported by the dock 134 the actuator 132 is coupled to the agitation component 136. Different types of actuator 132 may be used, with corresponding different types of agitation component 136.

Figure 4:
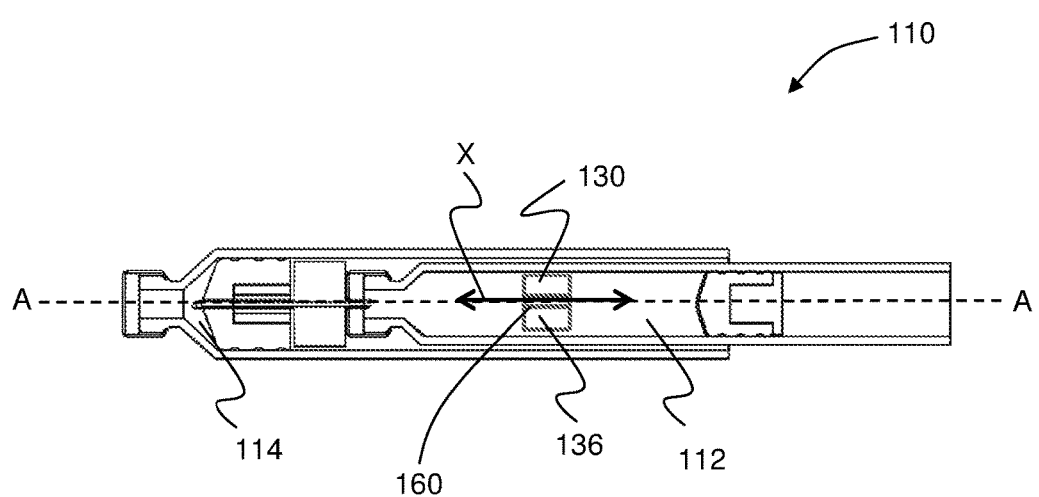
FIG. 4 is a cross-sectional view of a syringe for use with a mixing apparatus according to the embodiment of FIGS. 2 and 3.
Figure 5:
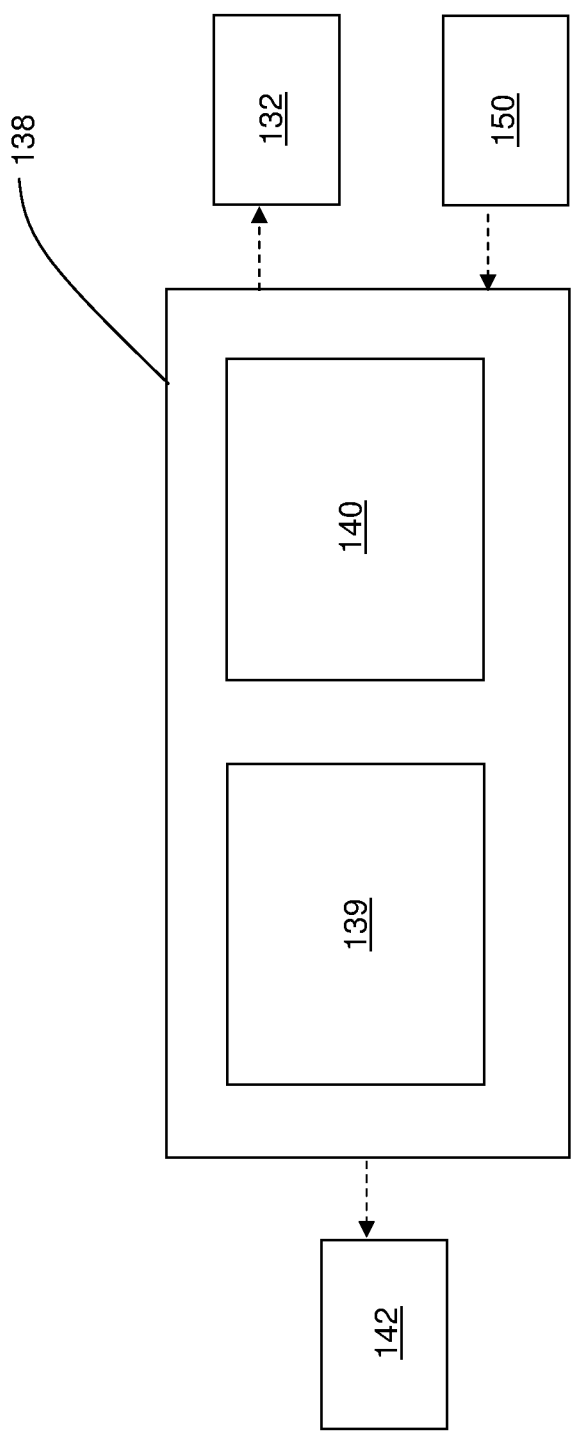
FIG. 5 is a schematic diagram of a control system of the mixing apparatus of FIGS. 2 and 3.
Figure 6:
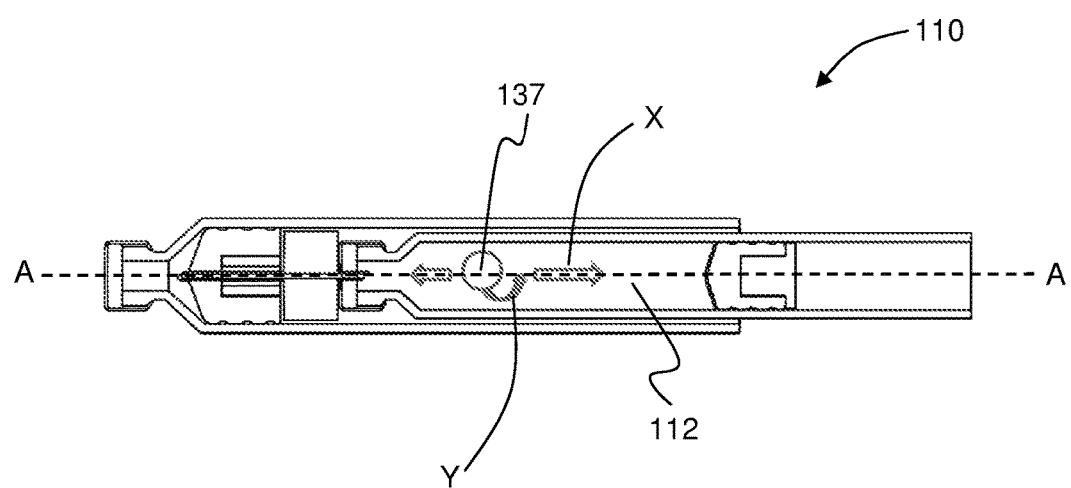
FIG. 6 is a cross-sectional view of a syringe for use with the mixing apparatus of FIGS. 2 and 3.

In this embodiment, the actuator 132 comprises a magnetic field, and the agitation component 136 is of a magnetic material or is a permanent magnet, preferably a rare earth high power permanent magnet. Such agitation components 136, 137 are shown in FIGS. 4 and 6.

Figure 3:
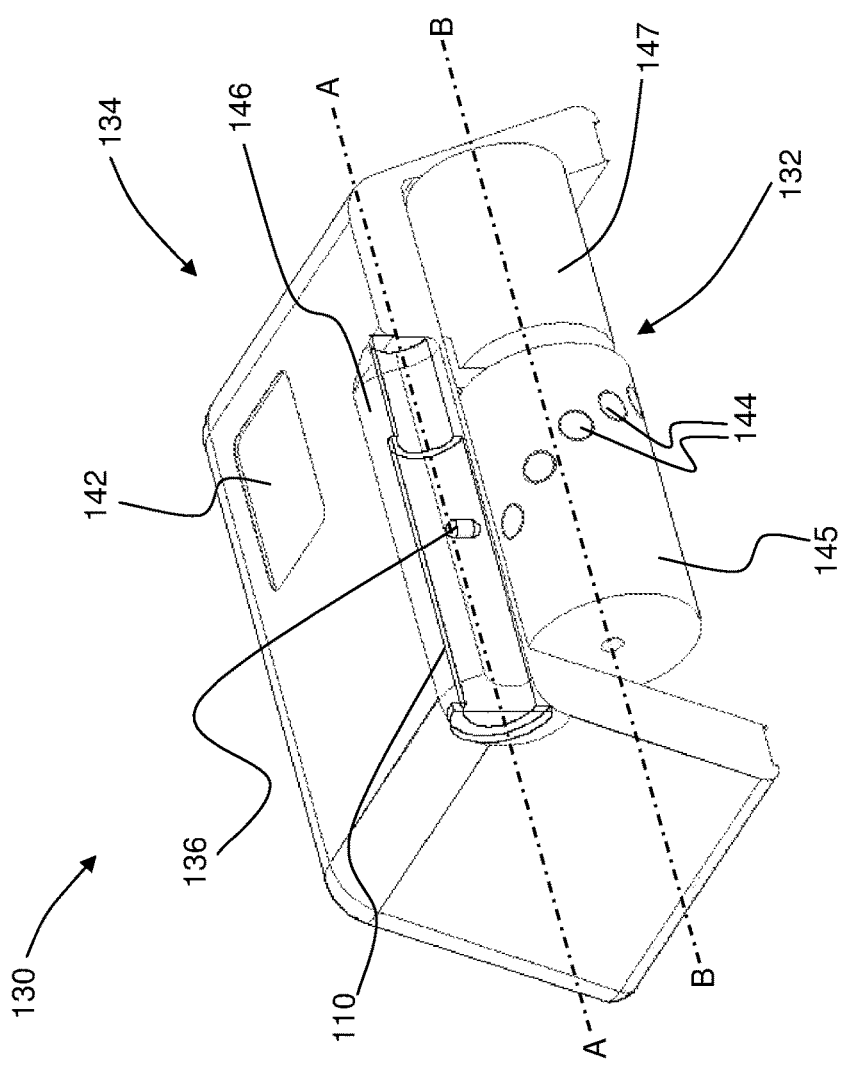
FIG. 3 is a partial cross-sectional perspective view through the mixing apparatus of FIG. 2.

The actuator 132 comprises a series of magnets, typically permanent magnets 144 attached to the cylindrical surface of a drum 145, as shown in FIG. 3. The magnets 144 are preferably rare earth high performance permanent magnets. The drum 145 is located in the dock 134 such that its longitudinal axis B-B is substantially parallel to axis A-A. The magnets 144 are offset in relation to one another relative to the axis B-B of the drum 145, and form a V-shape on the drum 145. The drum 145 is rotated about its axis B-B by a motor 147. As the drum 145 is rotated, each magnet 144 becomes closest to the agitation component 136, 137 in turn, and the agitation component 136, 137 is attracted to the closest magnet 144. The offset between the magnets 144 causes the agitation component 136, 137 to move along the axis A-A as it is attracted to each magnet 144 in turn. Reciprocating motion of the agitation component 136, 137 is thus achieved, as indicated by the arrow X in FIGS. 4 and 6.

The magnets 144 are arranged on the cylindrical surface of the drum 145 such that opposing poles are proximal one another. The agitation component 136, 137 is caused to spin (as shown by the arrow Y in FIG. 6) as the drum 145 rotates, due to the agitation component 136, 137 realigning itself with respect to the poles. Both agitation components 136, 137 can be reciprocated and/or rotated, and can be simultaneously reciprocated and rotated. The magnets 144 are spaced along the full length of the chamber 112, so that the agitation component 136, 137 is reciprocated along the full length of the chamber 112 and therefore sweeps through the whole volume thereof. This reduces the likelihood of unmixed substances collecting towards the ends of the chamber 112.

Further, the combination of spinning and longitudinal movement has been found to limit the frothing of certain medicaments which require mixing, if carried out in controlled conditions utilising the actuator described above. Certain medicaments have been found susceptible to this problem when shaken or mixed using known techniques.

In further variants two drums arranged at either side of the syringe of the type described above may be used in the dock, in conjunction with a single agitation component to further improve mixing. The agitation component jumps from being adjacent to one drum to being adjacent to the other. In this alternative embodiment, the agitation component 136 is reciprocated substantially perpendicular to the axis A-A, or in some other direction, due to a suitable alternative arrangement of the magnets 144. In this variant the agitation component can be arranged to move in a combined manner that includes spinning, reciprocating and moving across the syringe.

In an alternative embodiment the actuator 132 is a magnetic field provided by one or more electromagnets, e.g. a combination electrically switching electromagnets or by some other suitable type of magnet arrangement.

With reference to FIG. 4, the agitation component 136 is substantially cylindrical, and defines a bore 160 extending through the agitation component 136 substantially parallel to the axis A-A. The bore 160 allows the chamber contents to pass through the agitation component 136. This allows the agitation component 136 to move more freely within the chamber 112, and improves mixing due to the chamber contents passing through the bore 160. In an alternative embodiment (not shown), the agitation component is substantially disc-shaped. A cylinder or disc-shaped agitation component minimises the contents left in the syringe 110 after expulsion, minimising waste.

The agitation component 137 of FIG. 6 is substantially spherical. In alternative embodiments (not shown), the agitation component is of a different shape, such as a tetrahedron, cube, propeller, triangular, oval, torpedo, cross or dumbbell shaped. Such shapes promote mixing within the chamber 112.

In alternative embodiments (not shown) the agitation component is placed in the chamber 114 rather that chamber 112 as shown.

The agitation component 136, 137 is manufactured from suitable magnetic material. For example, magnetic stainless steel, ferrous metals or paramagnetic materials may be used. The agitation component 136, 137 is coated or encapsulated in a material that is suitable for contact with pharmaceutical substances, i.e. will not react with pharmaceutical substances. Suitable coating materials include glass, suitable types of plastic, suitable polymers such as Parylene, PTFE or elastomer, rubber, stainless steel or plasma coating.

Figure 7:
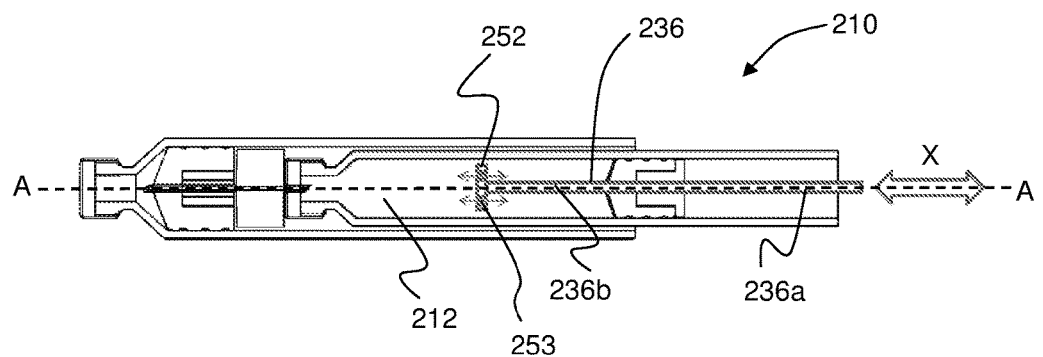
FIG. 7 is a cross-sectional view of a syringe with an agitation component according to a second embodiment of the invention.
Figure 8:
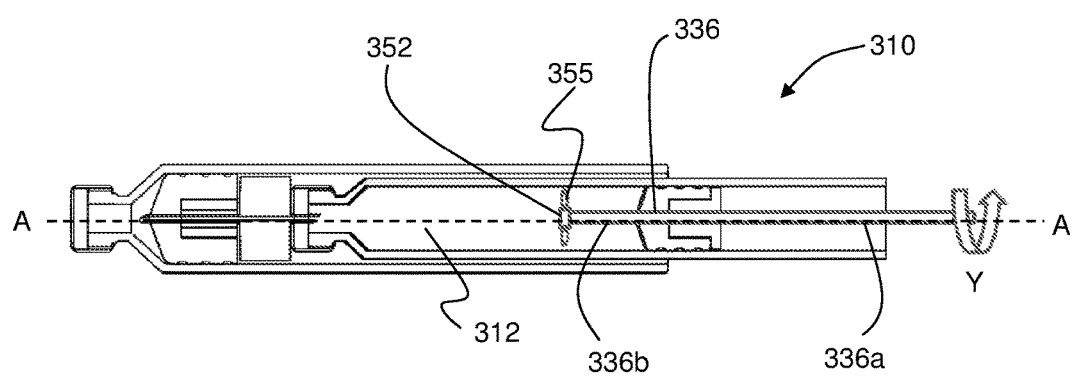
FIG. 8 is a cross-sectional view of a syringe with an agitation component according to a third embodiment of the invention.

A second embodiment of the invention is shown in FIG. 7. Features corresponding to those of the previous embodiments have been given corresponding reference numbers with the additional prefix "2". A third embodiment of the invention is shown in FIG. 8. Features corresponding to those of the previous embodiments have been given corresponding reference numbers with the additional prefix "3". Only features that differ from those of the first embodiment are discussed in more depth.

FIGS. 7 and 8 show agitation components 236, 336 configured for use with an actuator 132 in the form of a mechanical drive system, such as an electric motor (not shown). The agitation components 236, 336 are elongate, and have a first part 236a, 336a extending from the syringe 210, 310 and a second part 236b, 336b within the chamber 212, 312. When the syringe 210, 310 is received within a dock (not shown), the first part 236a, 336a is coupled with the motor which manipulates the agitation component 236, 336.

As with the previous embodiment, the agitation component 236, 336 can be moved in a reciprocating or a rotating motion. For example, the agitation component 236 is reciprocated substantially along axis A-A by the motor, as indicated by the arrow X of FIG. 7, and can be reciprocated along the length of the chamber 212, again reducing the likelihood of unmixed substances collecting towards the ends of the chamber 212. The agitation component 336 is rotated about the axis A-A, as indicated by the arrow Y in FIG. 8.

Both agitation components 236, 336 can be reciprocated and/or rotated, and can be simultaneously reciprocated and rotated by a suitable motor. The agitation component 236, 336 can also be manipulated manually via the first part 236a, 336a.

The agitation components 236, 336 have at their second part 236b, 336b an agitation component head 252, 352 configured to increase mixing. The agitation component head 252 of the agitation component 236 is cylindrical, and is co-axial with the remainder of the agitation component 236. The agitation component head 252 defines two bores 253 extending through the head 252 substantially parallel to the axis A-A. The bores 253 allow the chamber contents to pass through the agitation component 236. This allows the agitation component 236 to move more freely within the chamber 212, and improves mixing due to the chamber contents passing through the bores 253.

The agitation component head 352 of the agitation component 336 comprises a series of projections 355 extending substantially perpendicular to the axis A-A. The agitation component heads 252, 352 increase the proportion of the cross-sectional area of the chamber 212, 312 taken up by the agitation component 236, 336, thus improving mixing.

Different types of agitation component movement are selected by the operator using the buttons, or are automatically selected by the control system according to the syringe contents, as different types of mixing movement may suit different substances. A combination of rotation and reciprocation of the agitation components 136, 137, 236, 336 can be used.

Figure 9A:
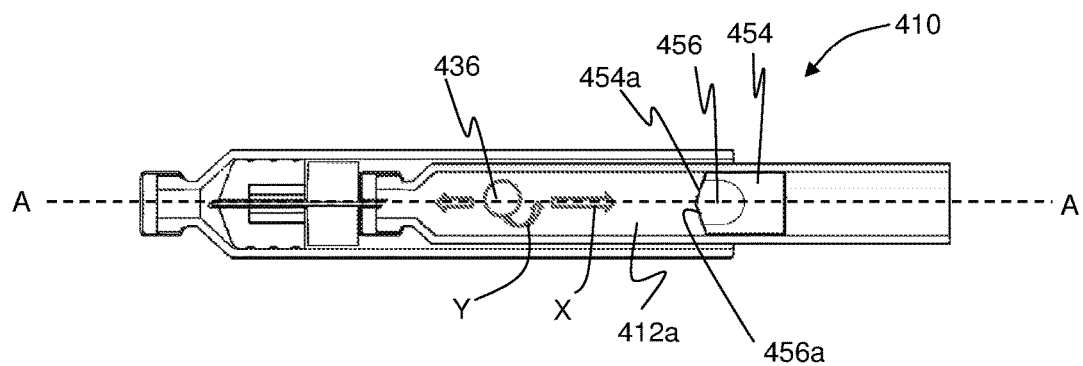
FIG. 9a is a cross-sectional view of a syringe according to a fourth embodiment of the invention in a first position.
Figure 9B:
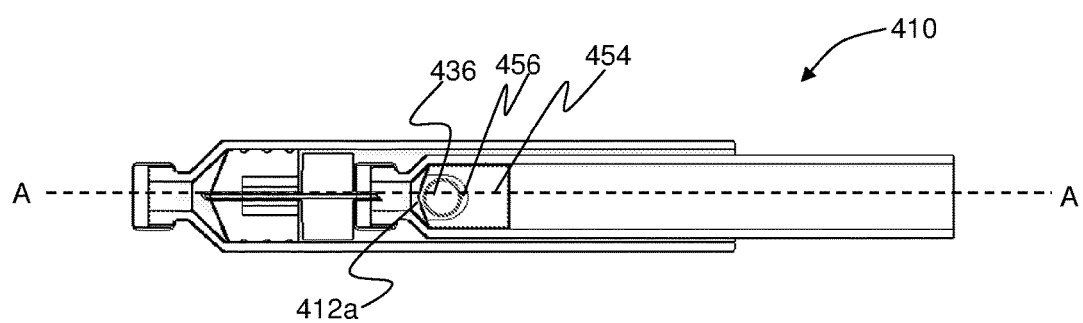
FIG. 9b is a cross-sectional view of the syringe of FIG. 9a in a second position.

A fourth embodiment of the invention is shown in FIGS. 9a and 9b. Features corresponding to those of the previous embodiments have been given corresponding reference numbers with the additional prefix "4". Only features that differ from those of the first embodiment are discussed in more depth.

The syringe 410 includes a plunger 454 configured to expel the contents of the chamber 412 from the syringe. The plunger 454 has a first end 454a defining the end of the chamber 412.

In this embodiment the agitation component 436 is of the same type as the agitation component 136 of FIG. 4, i.e. substantially spherical, of magnetic material, and configured to be manipulated by a magnetic field.

The shapes of the plunger 454 and agitation component 436 correspond to one another, and are intended to maximise the amount of substance that can be expelled from the syringe 410, and thus reduce waste.

The plunger 454 defines a recess 456 at its first end 454a. The recess 456 is U-shaped in cross section, with the open end 456a of the U opening into the chamber 412. The recess 456 is intended to receive the agitation component 436.

In the first position shown in FIG. 9a, the agitation component 436 is free to move within the chamber 412, and mixing is taking place. Once mixing has finished, the plunger 454 will be moved by the operator to decrease the size of the chamber 412 and thus expel the chamber contents from the syringe 410. As the plunger 454 approaches an outlet end 412a of the chamber, the agitation component 436 enters the recess 456. In an alternative embodiment (not shown), the recess 456 is outwardly tapered, in order to guide the agitation component 436 into the recess 456. In this embodiment, the recess 456 is configured to wholly receive the agitation component 436, although in alternative embodiments the recess 456 may be configured to only partially receive the agitation component 436. The agitation component 436 is thus prevented from acting as a stop between the plunger 454 and the end 412a of the chamber 412, allowing as much of the syringe contents as possible to be expelled from the syringe 410.

In a further embodiment (not shown) the agitation component can be designed such that is it substantially the same shape as the neck of the chamber or cartridge (i.e. the smaller diameter portion at the opposing end to the plunger), or smaller, such that it enters this volume during expulsing of the syringe contents, but nevertheless does not block the liquid from being expulsed. This allows as much of the syringe contents as possible to be expelled from the syringe.

Figure 10A:
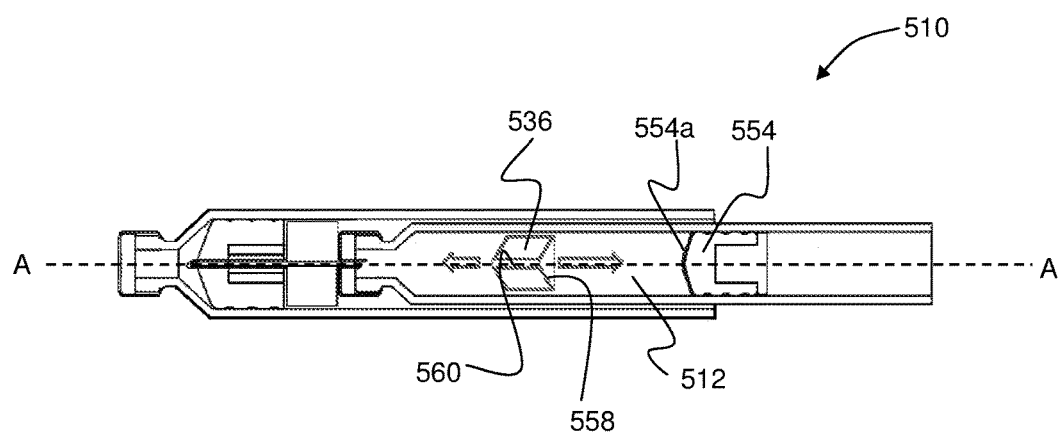
FIG. 10a is a cross-sectional view of a syringe according to a fifth embodiment of the invention in a first position.
Figure 10B:
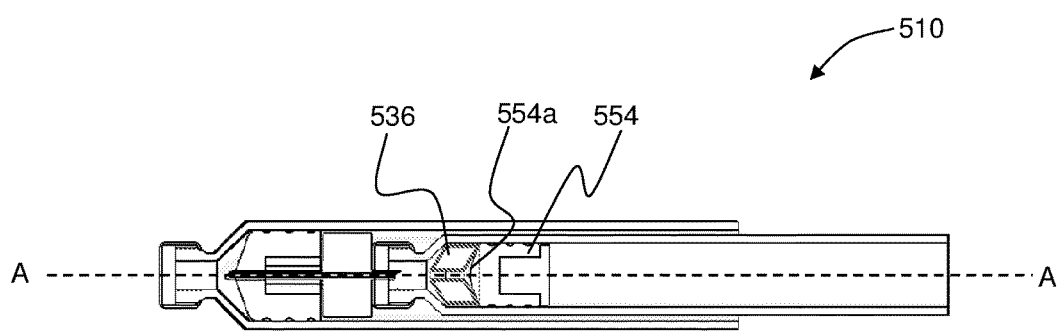
FIG. 10b is a cross-sectional view of the syringe of FIG. 10a in a second position.

A fifth embodiment of the invention is shown in FIGS. 10a and 109b. Features corresponding to those of the previous embodiments have been given corresponding reference numbers with the additional prefix "5". Only features that differ from those of the first embodiment are discussed in more depth.

The syringe 510 of this embodiment again has a corresponding plunger 554 and agitation component 536 intended to reduce waste. In this embodiment, the agitation component 536 defines a conical recess 558. The plunger 554 has a conical first end 554a corresponding to the recess 558. As the plunger 554 is moved towards the outlet end 512a of the chamber, its first end 554a enters the recess 558. The agitation component 536 acts as an extension of the plunger 554 and is moved towards the outlet end 512a with the plunger 554, expelling the chamber contents from the syringe 510 as it is moved. As much of the syringe contents as possible are thus expelled from the syringe 510.

In an alternative embodiment (not shown) a recess configured to partially or wholly receive the agitation component is defined by the chamber. In this embodiment, the agitation component is received into the chamber recess as the plunger moves towards the outlet end, so does not act as a stop between the plunger and the outlet end of the chamber.

In a further alternative embodiment (not shown), the agitation component is deformable and/or collapsible. The agitation component shapes itself to the plunger as the plunger is moved towards the outlet end of the chamber, thus preventing waste.

The agitation component 536 of this embodiment defines a bore 560 extending through the agitation component 536 substantially parallel to the axis A-A. The bore 560 allows the chamber contents to pass through the agitation component 536. This allows the agitation component 536 to move more freely within the chamber 512, and improves mixing due to the chamber contents passing through the bore 560. In other embodiments (not shown) the agitation component may have more than one bore extending through it, or may comprise a mesh, to improve movement of the agitation component and increase mixing.

Figure 11:
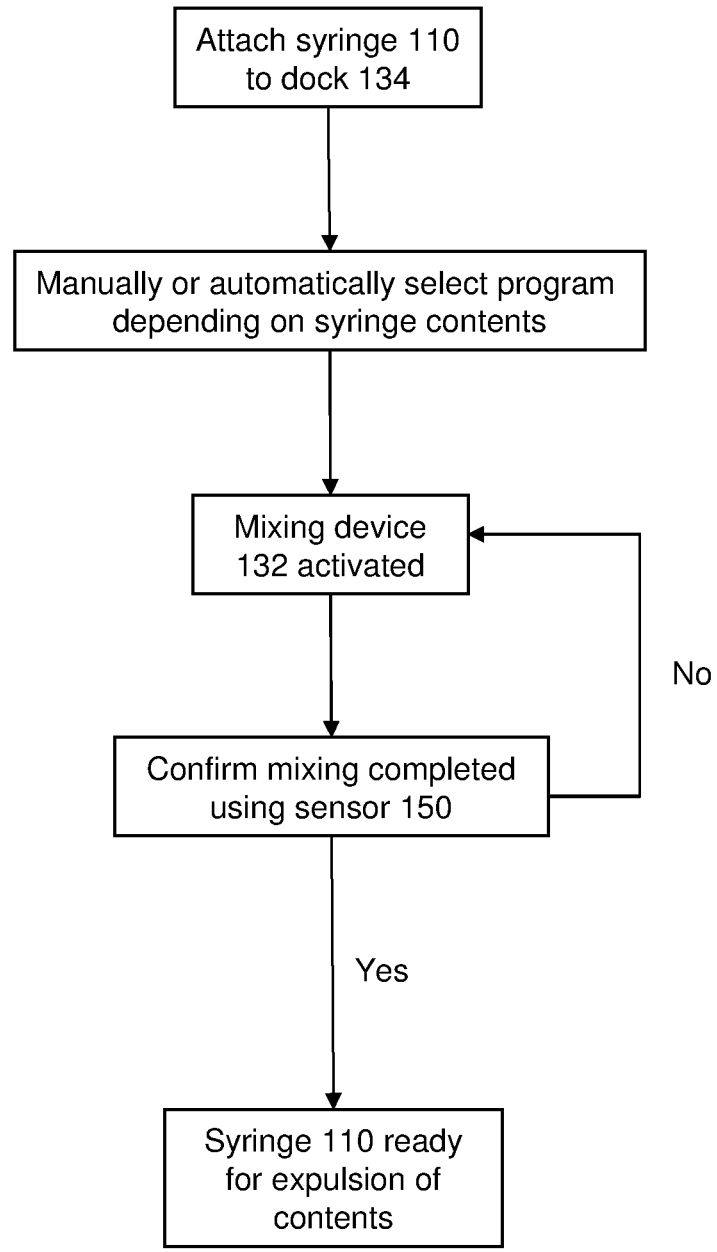
FIG. 11 is a flow diagram of a method according to an embodiment of the present invention.

A method of mixing a substance within a chamber 112 of a syringe 110 is shown in FIG. 11. The syringe 110 is operated so that the contents of the chamber 112, 114 are combined. The syringe 110, installed with a suitable agitation component 136, 137, is attached to the dock 134. A suitable program is selected by the operator depending on the syringe contents, and the control system 138 activates the actuator 132. After a predetermined length of time, the sensor 150 is used to confirm whether sufficient mixing has taken place. If not, the actuator 132 is activated again. Once sufficient mixing has taken place, the display 142 indicates that mixing is completed, and that the syringe 110 is ready for its contents to be expelled. In an alternative embodiment, the dock 134 may emit sounds indicating that mixing is complete, or that mixing is incomplete and the actuator 132 must be re-activated.

The mixing apparatus 130 allows reliable, controlled mixing of syringe contents, even when used by an unskilled operator. The dock 134 provides a secure location for mixing, and allows simple coupling of the syringe to the mixing apparatus 130.

The mixing apparatus 130 is suitable for use with types of syringe other than that described in the specific embodiment. For example, it is compatible with standard single-chamber syringes, or with more complex auto-injectors. It is also compatible with other types of dual-chamber syringe, e.g. where a bypass arrangement rather than a double-ended needle is used to combine the contents of the chambers. The mixing apparatus is also suitable for use with a syringe having a first chamber proximal an outlet end of said syringe and a second chamber distal said outlet end of said syringe, wherein the agitation component is configured for location within said second chamber. Accordingly, the term "syringe" as used in the claims should be understood to include any similar injection device or syringe cartridge which is, formed at least in part from one or more elongate typically cylindrical chamber(s). It will be appreciated by those well versed in the art that the claims can also apply to mixing in a vial prior to injection. The term "syringe" can also be used to mean "vial".

In alternative embodiments (not shown), all or part of the mixing apparatus may be permanently, semi-permanently or temporarily attached to or part of a syringe, or may be an integral part of a syringe. A power source may also be included in the mixing apparatus. For example, the actuator may be a sleeve comprising one or more magnets that fits over the chamber(s) of a disposable or refillable syringe. Alternatively, the actuator may itself comprise a syringe, which may be refillable, for example with one or more cartridges. The mixing apparatus may include more than one agitation component.

What is claimed is:

1. A mixing apparatus for a syringe, the mixing apparatus comprising:
   a dock configured to receive the syringe and having an agitation component actuator integral to the dock configured for magnetically coupling to an agitation component of a magnetic material located within a chamber of said syringe, and configured for manipulation of said agitation component within said chamber when coupled;
   such that the actuator is coupled to said agitation component when said syringe is received by the dock,
   wherein said chamber defines a longitudinal axis, wherein the actuator is in the form of a drum having a series of magnets attached thereto offset in relation to one another so as to manipulate an actuation component in a reciprocating motion along the longitudinal axis upon rotation of the drum,
   wherein the actuator is configured to rotate the agitation component about the longitudinal axis; and
   wherein the series of magnets are configured such that opposing poles are proximal one another to induce rotation of the agitation component, due to the agitation component realigning itself with respect to the poles.

2. The apparatus according to claim 1, wherein the series of magnets form a V-shape arrangement on the drum.

3. The apparatus according to claim 1 wherein the actuator is configured to manipulate said agitation component in a reciprocating motion substantially parallel with the chamber longitudinal axis.

4. The apparatus according to claim 3, wherein the drum defines a longitudinal axis that is substantially parallel to the chamber longitudinal axis.

5. The apparatus according to claim 1, further comprising a control system configured to control at least one of the following parameters: speed of movement of said agitation component; direction of movement of said agitation component; force or torque of said agitation component and length of mixing time.

6. The apparatus according to claim 1, wherein the dock is configured to retain said syringe until mixing is complete.

7. The apparatus according to claim 1 further comprising a sensor arrangement configured to detect a characteristic of contents of said chamber in order to determine a level of mixing of the contents.

8. The apparatus according to claim 7, wherein the sensor arrangement is configured to detect a characteristic of said chamber contents when said syringe is received by the dock.

\* \* \* \* \*